United States Patent [19]

Motola et al.

[11] Patent Number: 5,185,373
[45] Date of Patent: Feb. 9, 1993

[54] INHIBITION OF THERMAL DEGRADATION OF IBUPROFEN

[75] Inventors: Solomon Motola, Marlton; Robert G. Blank, Hammonton; Alan R. Branfman, Cherry Hill, all of N.J.

[73] Assignee: American Home Products Corporation, New York, N.Y.

[21] Appl. No.: 744,144

[22] Filed: Aug. 13, 1991

[51] Int. Cl.$^5$ ............................................. A61K 31/19
[52] U.S. Cl. .................................................... 514/570
[58] Field of Search .................................. 514/557, 570

[56] References Cited

U.S. PATENT DOCUMENTS 4,427,670  1/1984  Ofuchi et al. ...................... 514/174
4,436,738  3/1984  Bequette et al. ................... 514/174

OTHER PUBLICATIONS

Chem. Abstracts, vol. 114, p. 444, 254042t, Nakagawa et al.
Dondoni et al. "Studies on the Actual and Potential Impurities in Ibuprofen".

*Primary Examiner*—S. J. Friedman
*Attorney, Agent, or Firm*—John W. Routh

[57] ABSTRACT

The invention provides ibuprofen and ibuprofen containing pharmaceutical preparations stabilized against thermal degradation by the presence of a phenolic type antioxidant.

4 Claims, No Drawings

INHIBITION OF THERMAL DEGRADATION OF IBUPROFEN

FIELD OF INVENTION

This invention relates to the inhibition of the thermal degradation of ibuprofen. More particularly this invention relates to ibuprofen compositions for therapeutic administration inhibited against thermal degradation by incorporation therein of an antioxidant such as butylated hydroxytoluene, butylated hydoxyanisole and propyl gallate.

BACKGROUND OF THE INVENTION

The thermal stability of ibuprofen containing pharmaceutical preparations is important and closely monitored in order to maintain the pharmaceutical potency of the preparations. In particular, at least two thermal degradation products of ibuprofen are known, i.e. 4-isobutylacetophenone (IBAP) and 2-[4-isobutyrylphenyl)-propionic acid (IBRPP), and thermal stability studies normally include an assay for these degradation products. In preparation of certain ibuprofen containing pharmaceutical compositions, the ibuprofen and/or the composition containing the ibuprofen is heated to temperatures near 75°-77° C., the melting point of ibuprofen. For example, European Patent Application Publication Number 0 305 356 describes a granulation process wherein a drug powder, such as ibuprofen powder, is coated with a melt of ibuprofen to form the granulate. The melt in general has a temperature 10°-20° C. above the melting point of the product but the granules are rapidly chilled such that the increase in their temperature is limited to only 5°-10° C. for at most 30 seconds.

DESCRIPTION OF PRIOR ART

A journal article by Dondeni et al entitled "Studies of The Actual And Potential Impurities in Ibuprofen" published in Il Farmaco—Ed. Pr. vol 41 fasc. 7 pages 237-244 (1985) describes the isolation and characterization of some degradation products of ibuprofen arising from thermal decomposition and chemical oxidation. Several degradation products were obtained by heating ibuprofen at 105°-110° C. in the presence of air or oxygen for 7 days and the authors state that ibuprofen is an oxygen sensitive compound which undergoes decomposition to several named products. These degradation products include 4-isobutyl acetophenone (which was the starting material) but did not include 2-[4-isobutyrylphenyl]- propionic acid.

U.S. Pat. No. 4,427,670 issued to Ofuchi et al describes skin preparations containing a corticosteroid, a phosphatide and butylhydroxyanisole and/or butylhydroxytolnene. The butylhydroxy derivatives are said to prevent very satisfactorily the phosphatide from coloring the skin preparation and keeping it very stable for a prolonged period of time.

U.S. Pat. No. 4,436,738 issued to Beguette et al describes the stabilization of the unexpected oxidation of estradiol by phenolic type antioxidants such as butylhydroxyanisole and butylhydroxytoluene.

SUMMARY OF THE INVENTION

According to this invention, ibuprofen and ibuprofen containing pharmaceutical preparations are stabilized against thermal degradation at temperatures near or above the melting point of ibuprofen by the presence of a thermal degradation inhibiting amount of a phenolic type antioxidant such as butylhydroxytoluene, butylhydroxyanisole and propyl gallate. The phenolic type antioxidant is present in an amount of about 0.5 to about 3% by weight of the ibuprofen to be stabilized.

DETAILS OF THE INVENTION

The ibuprofen containing pharmaceutical preparations to be stabilized in accordance with this invention are those that during their manufacture or storage are or may be subjected to temperatures of the order of about 70° C. to about 85° C. or higher. Such preparations can be heated during manufacture by compression, by admixture with other heated or molten materials, and the like and the ibuprofen itself may be melted. Accordingly the pharmaceutical preparations to be stabilized include tablets, caplets, liquid formulations for pediatric/geriatric use, topical preparations including lotions, creams, gels and suppositories, and the like. Note for example U.S. Pat. No. 4,904,477 wherein the exit air temperature is 60°-65° C. from a spray dryer charged with a mixture containing ibuprofen. Also preparations manufactured from melted ibuprofen are made more practical since they retain potency.

Antioxidants useful in the present invention include t-butylhydroquinone, di-t-amylhydroquinone, di-t-butylhydroquinone, butylhydroxytolnene, butylhydroxyanisolepyrocatechol, pyrogallal, propyl gallate and nordihydroguaiaretic acid. The preferred antioxidants are butylhydroxyanisole butylhydroxytolnene and propyl gallate.

In order to illustrate the efficacy of the phenolic type antioxidants in stabilizing ibuprofen a study was conducted with ibuprofen, ketoprofen and flurbiprofen.

Samples of each compound and admixtures of each with butylhydroxytoluene (BHT), butylhydroxyanisole (BHA), and propyl gallate were prepared and stored at elevated temperatures, the ibuprofen samples at 80° C., the ketoprofen (mp.94° C.) samples at 120° C. and the flurbiprofen (m.p. 110°-111° C.) samples at 120° C. Samples were withdrawn at selected time intervals and analyzed by high performance liquid chromatography (HPLC). In the absence of antioxidants, a loss of both ibuprofen and flurbiprofen was observed. The HPLC chromatograms of ibuprofen show the presence of the two known degradation products, namely 2-(4-isobutyrylphenyl)-propionic acid and 4-isobutylacetophenone. The HPLL chromatograms of flurbiprofen did not show any extraneous peaks. No significant loss of ketoprofen was observed. The addition of antioxidants inhibits the degradation of ibuprofen but not that of flurbiprofen.

The high pressure liquid chromatography results are shown in the following table.

TABLE 1

| | HPLC ASSAY RESULTS | | |
|---|---|---|---|
| OVEN TEMPERATURE Hours | IBUPROFEN 80° C. % Found | KETO-PROFEN 120° C. % Found | FLURBI-PROFEN 120° C. % Found |
| 24 | 100 | 99.5 | 99.3 |
| 48 | 98.1 | 99.9 | 97.3 |
| 72 | 95.5 | 98.9 | 97.4 |
| 96 | — | — | 94.6 |
| 120 | 90.3 | — | — |
| 144 | 88.4 | 100 | — |
| 168 (1 Week) | — | 101 | 88.3 |
| ±1% BHT | | | |

TABLE 1-continued

HPLC ASSAY RESULTS

| OVEN TEMPERATURE Hours | IBUPROFEN 80° C. % Found | KETO-PROFEN 120° C. % Found | FLURBI-PROFEN 120° C. % Found |
| --- | --- | --- | --- |
| 24 | 99.4 | | 97.1 |
| 48 | 98.6 | | 95.3 |
| 72 | 98.4 | | 95.4 |
| 96 | — | | 95.5 |
| 120 | 98.0 | | — |
| 144 | 97.9 | | — |
| 168 | — | | 87.6 |
| +1% BHA | | | |
| 24 | 99.2 | | 97.0 |
| 48 | 98.1 | | 94.5 |
| 72 | 102 | | 93.9 |
| 96 | — | | 93.4 |
| 120 | 103 | | — |
| 144 | 104 | | — |
| 168 | — | | 88.2 |
| +1% Propyl Gallate | | | |
| 24 | 99.6 | | 97.4 |
| 48 | 98.3 | | 95.4 |
| 72 | 98.2 | | 94.4 |
| 96 | — | | 92.5 |
| 120 | 98.0 | | — |
| 144 | 98.1 | | — |
| 168 | — | | 88.3 |

— not determined

We claim:

1. A pharmaceutical composition containing ibuprofen stabilized against thermal degradation at temperatures near or above the melting point of ibuprofen by admixture therewith of a thermal degradation inhibiting amount of a phenolic type antioxidant selected from the group consisting of butylhydroxytoluene, butylhydroxyanisole and propyl gallate.

2. The composition of claim 1 wherein the phenolic type antioxidant is present in an amount of about 0.5 to about 3% by weight based on the weight of ibuprofen.

3. An admixture of ibuprofen and a thermal degradation inhibiting amount of a phenolic type antioxidant selected from the group consisting of butylhydroxytoluene, butylhydroxyanisole and propyl gallate.

4. The admixture of claim 3 wherein the phenolic type antioxidant is present in an amount of about 0.5 to about 3% by weight based on the weight of ibuprofen.

* * * * *